(12) United States Patent
Shankar et al.

(10) Patent No.: US 7,225,029 B2
(45) Date of Patent: May 29, 2007

(54) IMPLANTABLE CARDIAC THERAPY DEVICE WITH DUAL CHAMBER CAN TO ISOLATE HIGH-FREQUENCY CIRCUITRY

(75) Inventors: Balakrishnan Shankar, Valencia, CA (US); Matthew Whitlock, Chapel Hill, NC (US); Mark W. Kroll, Simi Valley, CA (US)

(73) Assignee: Pacesetter, Inc.

( * ) Notice: Subject to any disclaimer, the term of this patent is extended or adjusted under 35 U.S.C. 154(b) by 151 days.

(21) Appl. No.: 10/039,743

(22) Filed: Oct. 26, 2001

(65) Prior Publication Data

US 2003/0083719 A1    May 1, 2003

(51) Int. Cl.
*A61N 1/375*    (2006.01)
(52) U.S. Cl. ........................ 607/60; 128/903
(58) Field of Classification Search ................ 600/508, 600/509; 607/4, 5, 9, 30, 32, 36, 59, 60; 128/903
See application file for complete search history.

(56) References Cited

U.S. PATENT DOCUMENTS

| | | | |
|---|---|---|---|
| 4,314,562 A * | 2/1982 | Ware | 607/36 |
| 4,561,443 A | 12/1985 | Hogrefe et al. | |
| 4,681,111 A | 7/1987 | Silvian | |
| 5,058,581 A | 10/1991 | Silvian | |
| 5,113,869 A | 5/1992 | Nappholz et al. | |
| 5,342,408 A | 8/1994 | deCoriolis et al. | |
| 5,354,319 A | 10/1994 | Wyborny et al. | |
| 5,381,798 A | 1/1995 | Burrows | |
| 5,454,838 A | 10/1995 | Vallana et al. | |
| 5,496,351 A | 3/1996 | Plicchi et al. | |
| 5,496,361 A | 3/1996 | Moberg et al. | |
| 5,511,553 A | 4/1996 | Segalowitz | |
| 5,518,001 A | 5/1996 | Snell | |
| 5,544,661 A | 8/1996 | Davis et al. | |
| 5,562,713 A | 10/1996 | Silvian | |
| 5,617,871 A | 4/1997 | Burrows | |
| 5,674,249 A | 10/1997 | de Coriolis et al. | |
| 5,683,432 A | 11/1997 | Goedeke et al. | |
| 5,697,958 A * | 12/1997 | Paul et al. | 607/31 |
| 5,720,770 A | 2/1998 | Nappholz et al. | |
| 5,748,103 A | 5/1998 | Flach et al. | |
| 5,752,976 A | 5/1998 | Duffin et al. | |
| 5,814,091 A * | 9/1998 | Dahlberg et al. | 607/36 |
| 5,843,139 A | 12/1998 | Goedeke et al. | |
| 5,855,550 A | 1/1999 | Lai et al. | |
| 5,861,019 A * | 1/1999 | Sun et al. | 607/60 |
| 5,904,708 A | 5/1999 | Goedeke | |
| 5,944,659 A | 8/1999 | Flach et al. | |
| 5,999,848 A | 12/1999 | Gord et al. | |
| 6,004,276 A | 12/1999 | Wright et al. | |
| 6,009,350 A * | 12/1999 | Renken | 607/32 |

(Continued)

*Primary Examiner*—Robert E. Pezzuto
*Assistant Examiner*—Frances P. Oropeza

(57) ABSTRACT

An implantable cardiac therapy device is constructed with a housing that defines first and second chambers. The first chamber holds cardiac therapy circuitry, such as sensing and/or stimulation circuitry. The second chamber holds high-frequency circuitry that transmits and receives high-frequency signals used in communication with external devices. The dual-chamber housing allows the implantable cardiac therapy device to handle high-frequency signals in an isolated environment, thereby enabling longer range telemetry, without interfering with the cardiac therapy circuitry. The implantable cardiac therapy device can be linked to a cardiac network of knowledge workers that evaluate the data generated by the device and provide instructions to remotely program the device.

6 Claims, 12 Drawing Sheets

U.S. PATENT DOCUMENTS

| | | | |
|---|---|---|---|
| 6,073,050 A * | 6/2000 | Griffith | 607/57 |
| 6,083,248 A | 7/2000 | Thompson | |
| 6,115,636 A | 9/2000 | Ryan | |
| 6,155,267 A | 12/2000 | Nelson | |
| 6,162,180 A | 12/2000 | Miesel et al. | |
| 6,200,265 B1 | 3/2001 | Walsh et al. | |
| 6,213,942 B1 | 4/2001 | Flach et al. | |
| 6,225,901 B1 | 5/2001 | Kail, IV | |
| 6,230,049 B1 | 5/2001 | Fischell et al. | |
| 6,234,973 B1 | 5/2001 | Meador et al. | |
| 6,238,492 B1 | 5/2001 | Nakanishi et al. | |
| 6,240,317 B1 | 5/2001 | Villaseca et al. | |
| 6,264,614 B1 | 7/2001 | Albert et al. | |
| 6,270,457 B1 | 8/2001 | Bardy | |
| 6,282,441 B1 | 8/2001 | Raymond et al. | |
| 6,301,504 B1 | 10/2001 | Silvian | |
| 6,312,378 B1 * | 11/2001 | Bardy | 600/300 |
| 6,315,721 B2 | 11/2001 | Schulman et al. | |
| 6,336,900 B1 | 1/2002 | Alleckson et al. | |
| 6,379,300 B1 * | 4/2002 | Haubrich | 600/300 |
| 6,567,703 B1 * | 5/2003 | Thompson et al. | 607/60 |
| 6,675,045 B2 * | 1/2004 | Mass et al. | 607/32 |
| 2002/0095195 A1 * | 7/2002 | Mass et al. | 607/60 |

* cited by examiner

IMPLANTABLE CARDIAC THERAPY DEVICE WITH DUAL CHAMBER CAN TO ISOLATE HIGH-FREQUENCY CIRCUITRY

TECHNICAL FIELD

The present invention generally relates to implantable cardiac therapy devices.

BACKGROUND

Implantable cardiac therapy devices (ICTDs) are implanted within the body of a patient to monitor, regulate, and/or correct heart function. ICTDs include implantable cardiac stimulation devices (e.g., implantable cardiac pacemakers, implantable defibrillators) that apply stimulation therapy to the heart as well as implantable cardiac monitors that monitor heart activity.

ICTDs typically include a control unit positioned within a casing that is implanted into the body and a set of leads that are positioned to impart stimulation and/or monitor cardiac activity. With improved processor and memory technologies, the control units have become increasingly more sophisticated, allowing them to monitor many types of conditions and apply tailored stimulation therapies in response to those conditions.

ICTDs are typically capable of being programmed remotely by an external programming device, often called a "programmer". Today, individual ICTDs are equipped with telemetry circuits that communicate with the programmer. One type of programmer utilizes an electromagnetic wand that is placed near the implanted cardiac device to communicate with the implanted device. The wand contains a coil that forms a transformer coupling with the ICTD telemetry circuitry. The wand transmits low frequency signals by varying coil impedance.

Early telemetry systems were passive, meaning that the communication was unidirectional from the programmer to the implanted device. Passive telemetry allowed a treating physician to download instructions to the implanted device following implantation. Due to power and size constraints, early commercial versions of the implanted devices were incapable of transmitting information back to the programmer.

As power capabilities improved, active telemetry became feasible, allowing synchronous bi-directional communication between the implanted device and the programmer. Active telemetry utilizes a half-duplex communication mode in which the programmer sends instructions in a predefined frame format and, following termination of this transmission, the implanted device returns data using the frame format. With active telemetry, the treating physician is able to not only program the implanted device, but also retrieve information from the implanted device to evaluate heart activity and device performance. The treating physician may periodically want to review device performance or heart activity data for predefined periods of time to ensure that the device is providing therapy in desired manner. Consequently, current generation implantable cardiac therapy devices incorporate memories, and the processors periodically sample and record various performance parameter measurements in the memories.

Current telemetry systems have limited communication range between the programmer wand and the ICTD, and are often referred to as "short-range telemetry" or "wand telemetry". For effective communication, the wand is held within a few inches of the ICTD. One problem is that the ICTD has insufficient power to transmit longer range signals. Another consideration is the inherent EMI-resistant design of the ICTD. The ICTD circuitry is typically housed in a hermetically shielded can to prevent electromagnetic interference (EMI) from disrupting operation. The can prevents penetration of high frequencies, thereby limiting communication to the low frequency range of less than 200 KHz. In one exemplary system, signals sent from the programmer to the implanted device are transmitted at approximately 36 KHz, and data is transmitted back from the implanted device to the programmer at approximately 8 KHz.

Conventionally, data about a patient's cardiac condition is gathered and stored by the programmer during programming sessions of the ICTDs. Analysis of the cardiac condition is performed locally by the programming software. Programmers offer comprehensive diagnostic capabilities, high-speed processing, and easy operation, thereby facilitating efficient programming and timely patient follow-up.

In addition to local analysis, TransTelephonic Monitoring (TTM) systems are employed to gather current cardiac data of patients when the patient is remote from the healthcare provider. TTM systems are placed in patients' homes. They typically include a base unit that gathers information from the ICTD much like the programmer would. The base unit is connected to a telephone line so that data may be transmitted to the medical staff responsible for that patient. An example of an ICTD TTM system is a service from St. Jude Medical® and Raytel® Cardiac Services called "Housecall™." This service provides current programmed parameters and episode diagnostic information for a plurality of events including stored electrograms (EGMs). Real-time EGMs with annotated status information can also be transmitted.

Using a telephone and a transmitter, the TTM system provides both the medical staff and the patient the convenience of instant analysis of therapy without having the patient leave the comfort of home. Typically, real-time measurements are transmitted in just minutes. Patients may be closely monitored, and the medical staff has more control of their patient's treatment, thus administering better patient management.

Although TTM systems monitor and transmit data for specific patients, the data is not collected and stored in the ICTD itself. Nor is the data collected and analyzed to determine therapy effectiveness or whether adjustment is desirable. On a basis of a patient population, there is no existing mechanism for gathering long-term and real-time data that includes cardiac monitoring and treatment information of a patient population and other medical and demographic information of a patient population.

Accordingly, there is a need for a more comprehensive system that communicates more effectively with the implanted cardiac therapy device over greater transmissions ranges.

SUMMARY

An implantable cardiac therapy device is constructed with a housing to hold both cardiac therapy circuitry and the high-frequency circuitry. In one implementation, the housing defines first and second chambers. The first chamber holds the cardiac therapy circuitry, such as sensing and/or stimulation circuitry. The second chamber holds the high-frequency circuitry, such as an RF transceiver, that transmits and receives high-frequency signals used in communication with external devices. The dual-chamber housing allows the implantable cardiac therapy device to handle high-frequency signals in an isolated environment, thereby enabling longer range telemetry, without interfering with the cardiac therapy circuitry. The implantable cardiac therapy device can further be linked to a cardiac network of knowledge workers that evaluate the data generated by the device and provide instructions to remotely program the device.

DETAILED DESCRIPTION

The following description is of the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like numerals or reference designators are used to reference like parts or elements.

Cardiac Therapy Network

Figure 1:
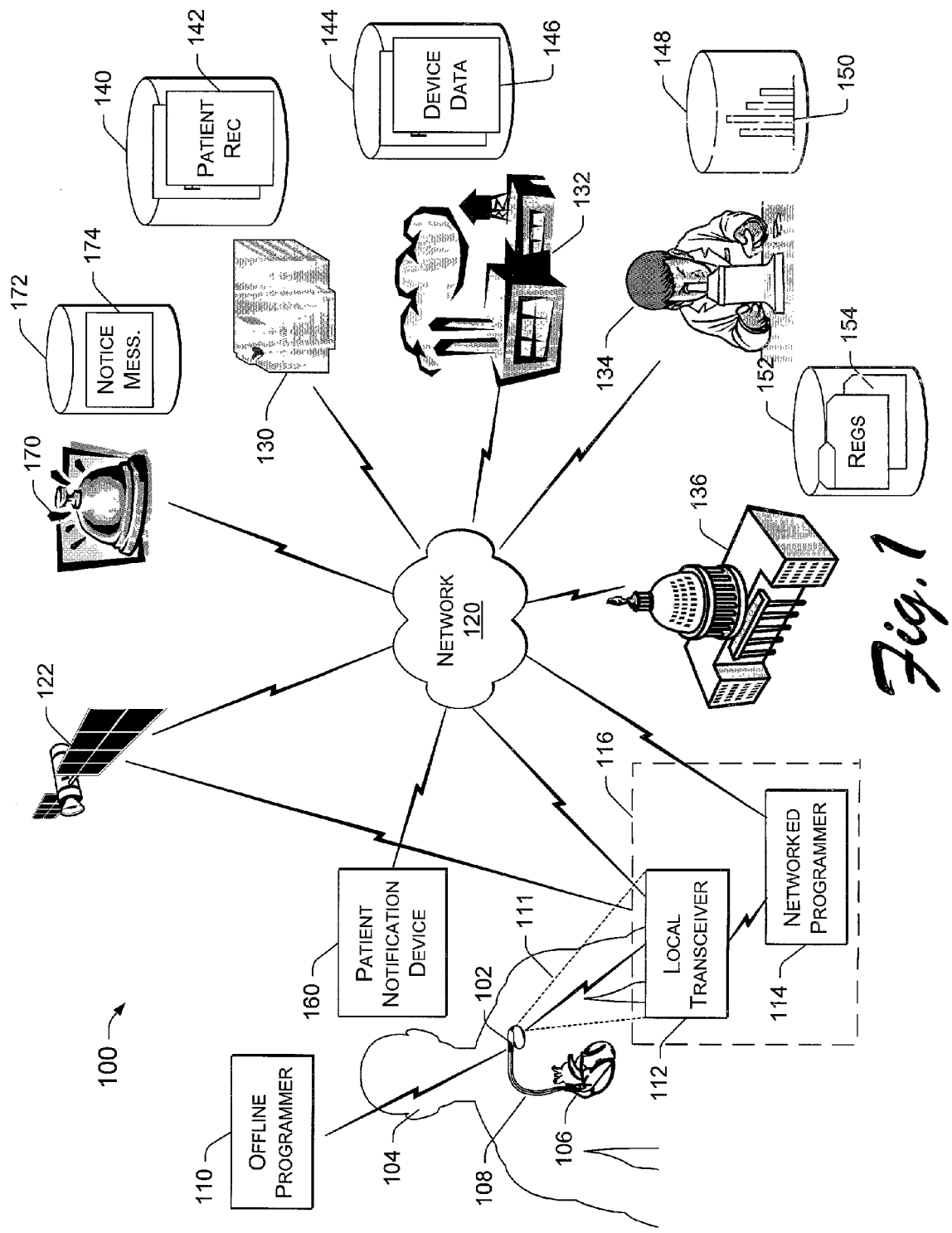
FIG. 1 is a diagrammatic illustration of a cardiac therapy network architecture with an implantable cardiac therapy device (ICTD) connected to a network of computing systems used by various knowledge workers.

FIG. 1 shows an exemplary cardiac therapy network architecture 100 that includes an implantable cardiac therapy device (ICTD) 102 coupled to a network of computing systems associated with various knowledge workers who have interest in cardiac therapy. The ICTD is illustrated as being implanted in a human patient 104. The ICTD 102 is in electrical communication with a patient's heart 106 by way of multiple leads 108 suitable for monitoring cardiac activity and/or delivering multi-chamber stimulation and shock therapy.

The ICTD 102 may communicate with a standalone or offline programmer 110 via short-range telemetry technology. The offline programmer 110 is equipped with a wand that, when positioned proximal to the ICTD 102, communicates with the ICTD 102 through a magnetic coupling.

The ICTD 102 can alternatively, or additionally, communicate with a local transceiver 112. The local transceiver 112 may be a device that resides on or near the patient, such as an electronic communications device that is worn by the patient or is situated on a structure within the room or residence of the patient. The local transceiver 112 communicates with the ICTD 102 using short-range telemetry or longer-range high-frequency-based telemetry, such as RF (radio frequency) transmissions. Alternatively, the local transceiver 112 may be incorporated into the ICTD 102, as represented by dashed line 111. In this case, the ICTD includes a separate and isolated package area that accommodates high-frequency transmissions without disrupting operation of the monitoring and stimulation circuitry.

Depending upon the implementation and transmission range, the local transceiver 112 can be in communication with various other devices of the network architecture 100. One possible implementation is for the local transceiver 112 to transmit information received from the ICTD 102 to a networked programmer 114, which is connected to network 120. The networked programmer 114 is similar in operation to standalone programmer 110, but differs in that it is connected to the network 120. The networked programmer 114 may be local to, or remote from, the local transceiver 112; or alternatively, the local transceiver 112 may be incorporated into the networked programmer 114, as represented by dashed line 116.

Another possible implementation is for the local transceiver to be connected directly to the network 120 for communication with remote computing devices and/or programmers. Still another possibility is for the local transceiver 112 to communicate with the network 120 via wireless communication, such as via a satellite system 122.

The network 120 may be implemented by one or more different types of networks (e.g., Internet, local area network, wide area network, telephone, cable, satellite, etc.), including wire-based technologies (e.g., telephone line, cable, fiber optics, etc.) and/or wireless technologies (e.g., RF, cellular, microwave, IR, wireless personal area network, etc.). The network 104 can be configured to support any number of different protocols, including HTTP (HyperText Transfer Protocol), TCP/IP (Transmission Control Protocol/Internet Protocol), WAP (Wireless Application Protocol), Bluetooth, and so on.

A number of knowledge workers are interested in data gathered from the implantable cardiac therapy device 102. Representative knowledge workers include healthcare providers 130, the device manufacturer 132, clinical groups 134, and regulatory agencies 136. The knowledge workers are interested in different portions of the data. For instance, the healthcare providers 130 are interested in information pertaining to a particular patient's condition. The manufacturer 134 cares about how the device is operating. The clinical groups 136 want certain data for inclusion in patient populations that can be studied and analyzed. The regulatory agencies 136 are concerned whether the devices, and various treatments administered by them, are safe or pose a health risk.

The network architecture 100 facilitates distribution of the device data to the various knowledge workers. Information gathered from the device is integrated, processed, and distributed to the knowledge workers. Computer systems maintain and store the device data, and prepare the data for efficient presentation to the knowledge workers. The computer systems are represented pictorially in FIG. 1 as databases. However, such system can be implemented s using a wide variety of computing devices, ranging from small handheld computers or portable digital assistants (PDAs) carried by physicians to workstations or mainframe computers with large storage capabilities. The healthcare providers 130 are equipped with computer systems 140 that store and process patient records 142. The manufacturer 132 has a computer system 144 that tracks device data 146 returned from ICTDs 102. The clinical groups 134 have computer systems 148 that store and analyze data across patient populations, as represented by a histogram 150. The regulatory agencies 136 maintain computer systems 152 that register and track healthcare risk data 154 for ICTDs.

The network architecture 100 supports two-way communication. Not only is data collected from the ICTD 102 and distributed to the various computer systems of the knowledge workers, but also information can be returned from these computer systems to the networked programmer 114 and/or the local transceiver 112 for communication back to the ICTD 102. Information returned to the ICTD 102 may be used to adjust operation of the device, or modify therapies being applied by the device. Such information may be imparted to the ICTD 102 automatically, without the patient's knowledge.

Additionally, information may be sent to a patient notification device 160 to notify the patient of some event or item. The patient notification device 160 can be implemented in a number of ways including, for example, as a telephone, a cellular phone, a pager, a PDA (personal digital assistant), a dedicated patient communication device, a computer, an alarm, and so on. Notifications may be as simple as an instruction to sound an alarm to inform the patient to call into the healthcare providers, or as complex as HTML-based pages with graphics and textual data to educate the patient. Notification messages sent to the patient notification device 160 can contain essentially any type of information related to cardiac medicinal purposes or device operation. Such information might include new studies released by clinical groups pertaining to device operation and patient activity (e.g., habits, diets, exercise, etc.), recall notices or operational data from the manufacturer, patient-specific instructions sent by the healthcare providers, or warnings published by regulatory groups.

Notifications can be sent directly from the knowledge worker to the patient. Additionally, the network architecture 100 may include a notification system 170 that operates computer systems 172 designed to create and deliver notification messages 174 on behalf of the knowledge workers. The notification system 170 delivers the messages in formats supported by the various types of patient notification devices 160. For instance, if the patient carries a pager, a notification message might consist of a simple text statement in a pager protocol. For a more sophisticated wireless-enabled PDA or Internet-oriented cellular phone, messages might contain more than text data and be formatted using WAP formats.

Figure 2:
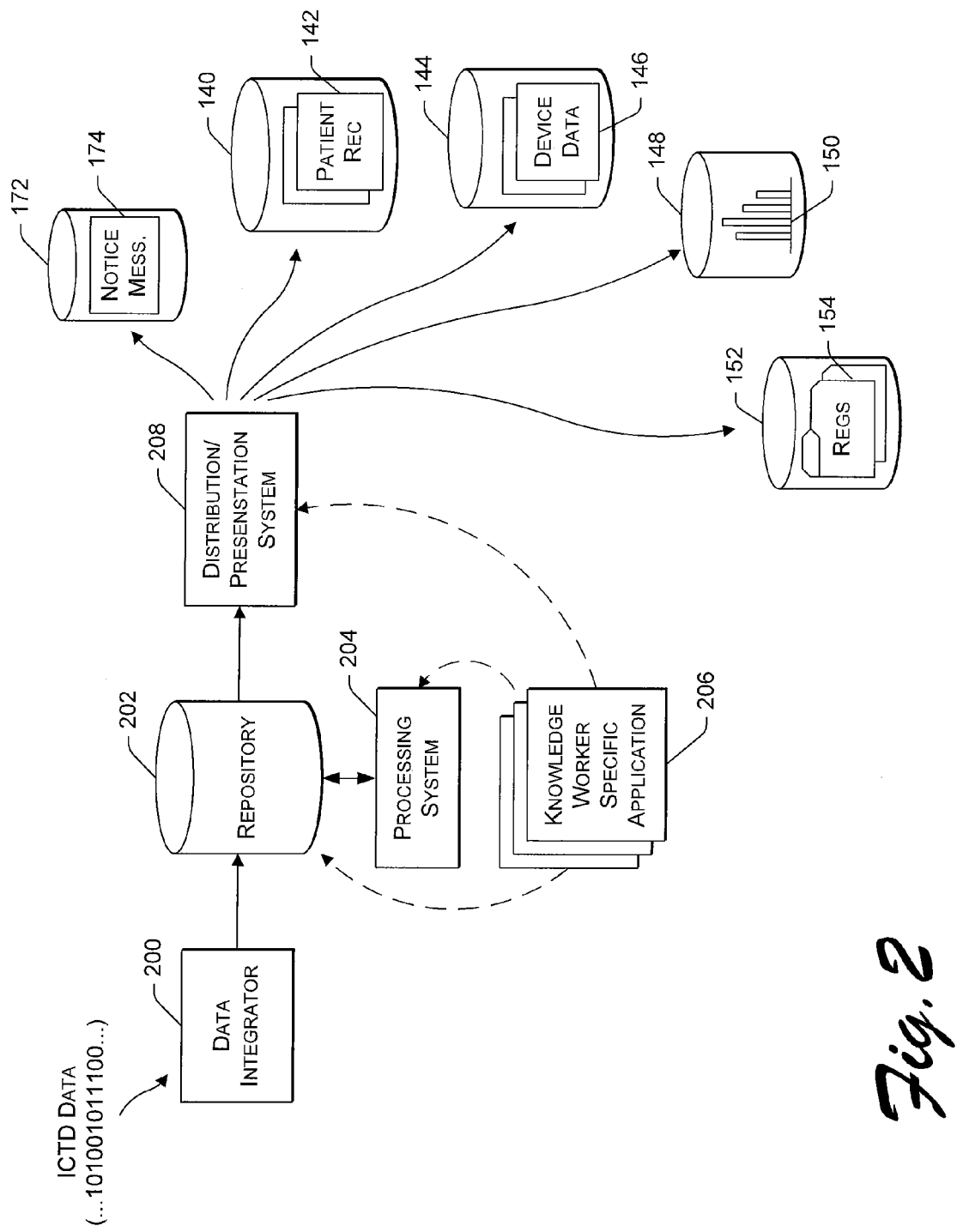
FIG. 2 is a functional diagram illustrating information flow from the ICTD to the computing systems associated with the knowledge workers.

FIG. 2 shows the flow of data from the implantable cardiac therapy device 102 to the various computer systems used by the knowledge workers. Data from the ICTD is output as digital data, as represented by the string of 0's and 1's. The data may consist of any number of items, including heart activity (e.g., ECG), patient information, device operation, analysis results from on-device diagnostics, and so on.

A data integrator 200 accumulates the data and stores it in a repository 202. A processing system 204 processes portions of the data according to various applications 206 that are specifically tailored to place the data into condition for various knowledge workers. For example, healthcare workers might be interested in certain portions of the data, such as the ECG data and the patient information. Clinical scientists might be interested in the heart data, but do not wish to see any patient information. Manufacturers may be interested in the raw data stream itself as a tool to discern how the device is operating. Depending on the needs of the end worker, the processing system 204 takes the raw device data, evaluates its accuracy and completeness, and generates different packages of data for delivery to the various knowledge workers. The processed data packages are also stored in the repository 202.

When the data is ready for delivery, a distribution/presentation system 208 distributes the different packages to the appropriate computer systems 140, 144, 148, 152, and 172. The distribution/presentation system 208 is configured to serve the packages according to the protocols and formats desired by the computer systems. In this manner, the network architecture 100 allows relevant portions of device data, collected from the ICTD, to be disseminated to the appropriate knowledge workers in a form they prefer.

Once the ICTD data is delivered, the computer systems 140, 144, 148, 152, and 172 store the data and/or present the data to the knowledge worker. The computer systems may perform further processing specific to their use of the data. Through these processes, the knowledge workers create additional information that is useful to the patient, or other knowledge workers with interests in ICTDs. For example, from the ICTD data, the knowledge workers might devise improved therapies for a given patient, or create instructions to modify operation of a specific ICTD, or gain a better understanding of how implantable cardiac devices operate in general, or develop better technologies for future generations of ICTDs. Much of this created knowledge can be shared among the various knowledge workers.

Figure 3:
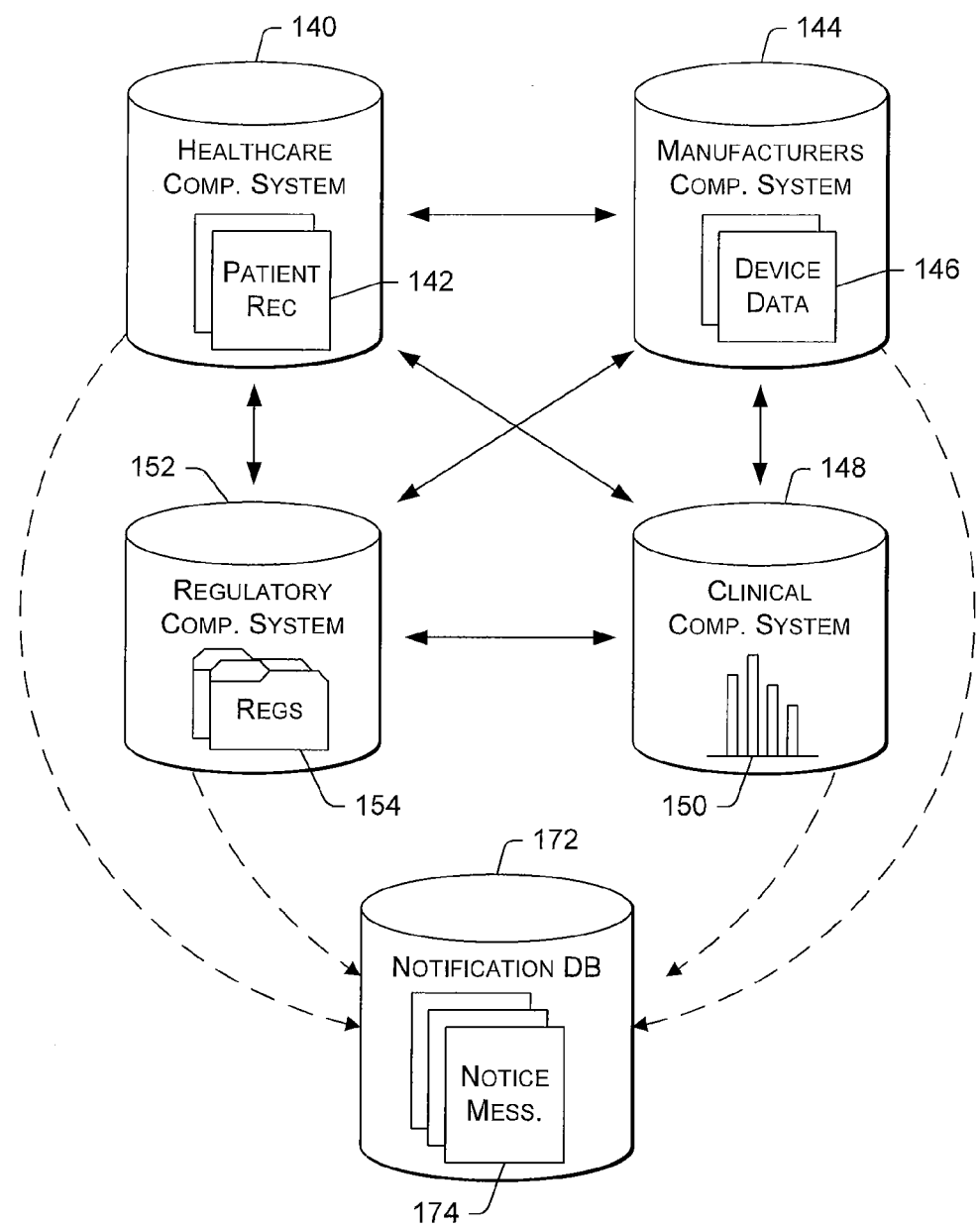
FIG. 3 is a functional diagram illustrating how the various computing systems share pieces of information to improve care given to the patient.

FIG. 3 shows how the various computing systems 140, 144, 148, 152, and 172 can cooperate and share pieces of information to improve the care given to a patient. Where appropriate and legally acceptable, the computer systems may be configured to pass non-private information among the various knowledge workers to better improve their understanding of the implantable medical field. Clinical results 150 produced by the clinical computer systems 148 may be shared with healthcare providers to improve patient care or with manufacturers to help in their design of next generation devices. The sharing of information may further lead to better and timelier healthcare for the patients.

If the collective knowledge base produces information that may prove helpful to the patient, that information can be passed to the notification system 172 for delivery to one or more patients. Also, any one of the knowledge workers may wish to employ the notification system 172 to send messages to the patient(s).

Figure 4:
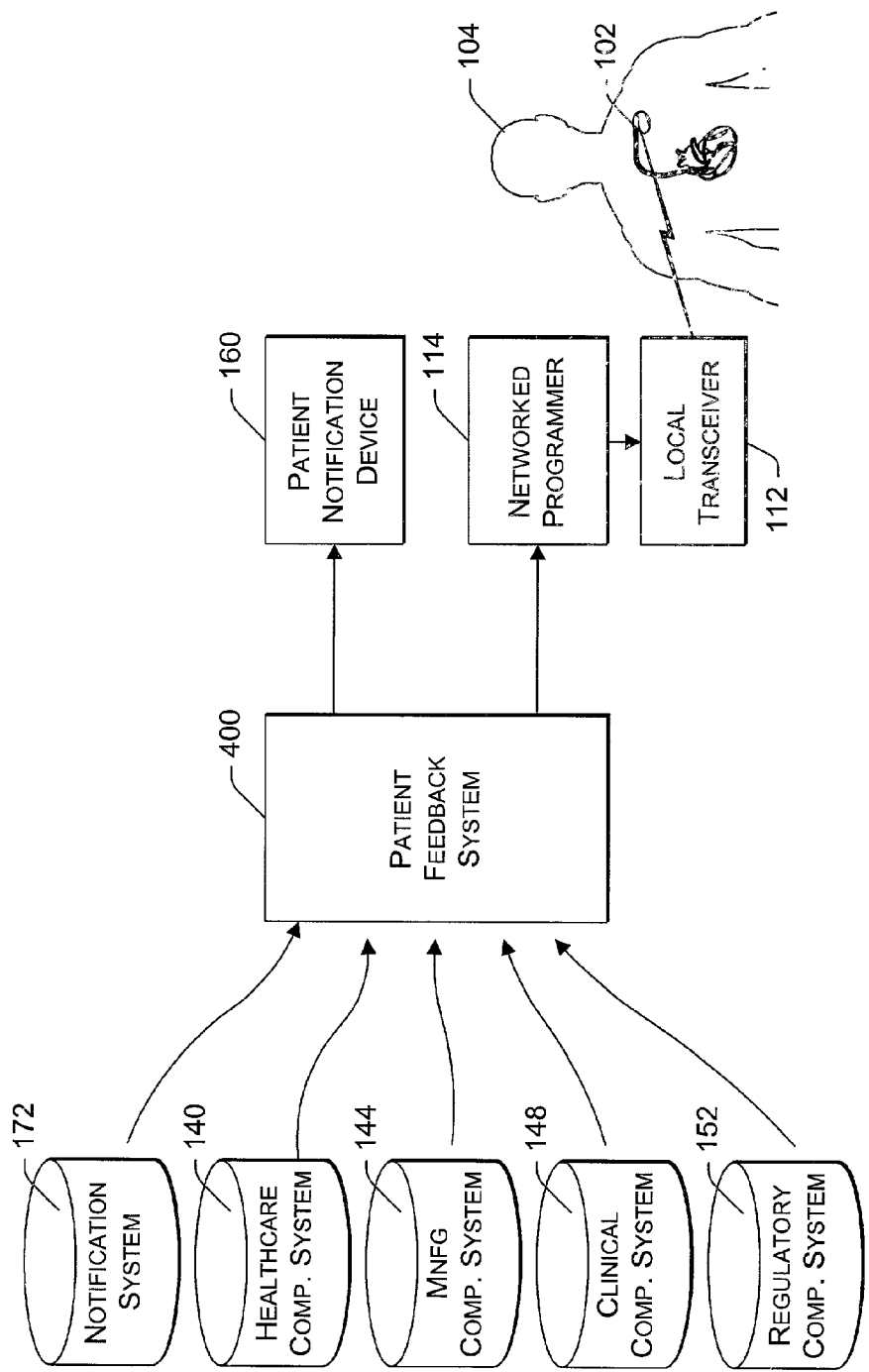
FIG. 4 is a functional diagram illustrating information flow from the computing systems back to the ICTD.

FIG. 4 shows, in more detail, the flow of information back from the various computer systems used by the knowledge workers to the implantable cardiac therapy device 102 or the patient notification device 160. Information from any one of the computing systems—healthcare computer system(s) 140, manufacturer computer system(s) 144, clinical computer system(s) 148, regulatory computer system(s) 152—or the notification system 172 can be sent to a patient feedback system 400. The patient feedback system 400 facilitates delivery of the information back to the patient. It may be an independent system, or incorporated into one or more of the computing. It may alternatively be integrated into the notification system 172.

The patient feedback system 400 may be implemented in many ways. As one exemplary implementation, the patient feedback system 400 is implemented as a server that serves content back to the networked programmer 114, which then uses the information to program the ICTD 102 either directly (e.g., via a proximally located wand) or via local transceiver 112. As another possible implementation, the patient feedback system may be a cellular or RF transmission system that sends information back to the patient feedback device 160.

The network architecture 100 facilitates continuous care around the clock, regardless of where the patient is located. For instance, suppose the patient is driving in the car when a cardiac episode occurs. The ICTD 102 detects the condition and transmits an alert message about the condition to the local transceiver 112. The message is processed and delivered to a physician's computer or PDA via the network 120. The physician can make a diagnosis and send some instructions back to the patient's ICTD. The physician might also have a notification message that guides the patient to a nearest healthcare facility for further treatment sent via the notification system 170 to the patient's notification device 160. Concurrently, the physician can share the patient's records online with an attending physician at the healthcare facility so that the attending physician can review the records prior to the patient's arrival.

Exemplary ICTD

Figure 5:
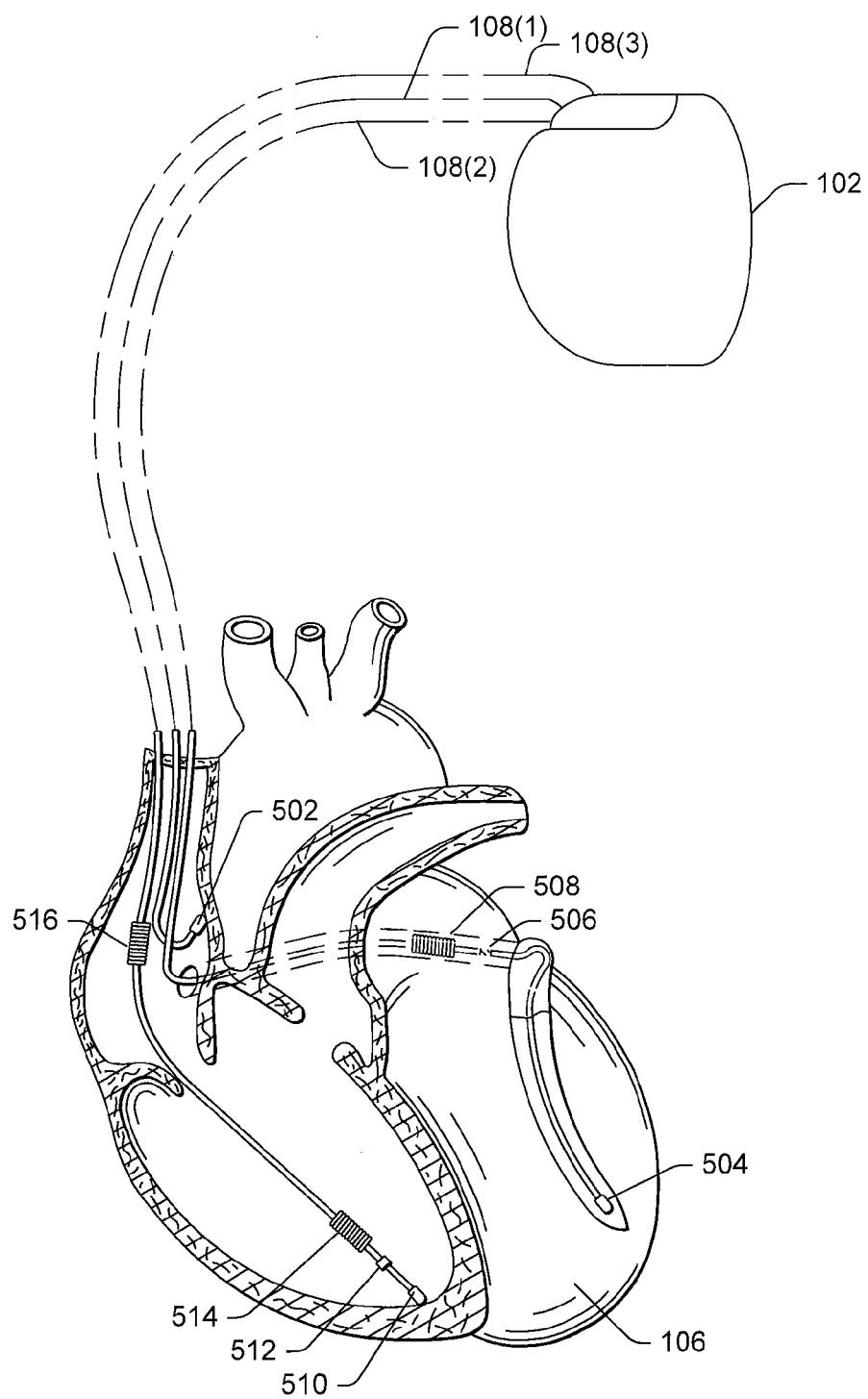
FIG. 5 is a simplified illustration of an ICTD in electrical communication with a patient's heart for monitoring heart activity and/or delivering stimulation therapy.

FIG. 5 shows an exemplary ICTD 102 in electrical communication with a patient's heart 106 for monitoring heart activity and/or delivering stimulation therapy, such as pacing or defibrillation therapies. The ICTD 102 is in electrical communication with a patient's heart 106 by way of three leads 108(1)-(3). To sense atrial cardiac signals and to provide right atrial chamber stimulation therapy, the ICTD 102 is coupled to an implantable right atrial lead 108(1) having at least an atrial tip electrode 502, which typically is implanted in the patient's right atrial appendage. To sense left atrial and ventricular cardiac signals and to provide left chamber pacing therapy, the ICTD 102 is coupled to a coronary sinus lead 108(2) designed for placement in the coronary sinus region via the coronary sinus. The coronary sinus lead 108(2) positions a distal electrode adjacent to the left ventricle and/or additional electrode(s) adjacent to the left atrium. An exemplary coronary sinus lead 108(2) is designed to receive atrial and ventricular cardiac signals and to deliver left ventricular pacing therapy using at least a left ventricular tip electrode 504, left atrial pacing therapy using at least a left atrial ring electrode 506, and shocking therapy using at least a left atrial coil electrode 508.

The ICTD 102 is also shown in electrical communication with the patient's heart 106 by way of an implantable right ventricular lead 108(3) having, in this implementation, a right ventricular tip electrode 510, a right ventricular ring electrode 512, a right ventricular (RV) coil electrode 514, and an SVC coil electrode 516. Typically, the right ventricular lead 108(3) is transvenously inserted into the heart 102 to place the right ventricular tip electrode 510 in the right ventricular apex so that the RV coil electrode 514 will be positioned in the right ventricle and the SVC coil electrode 516 will be positioned in the superior vena cava. Accordingly, the right ventricular lead 108(3) is capable of receiving cardiac signals, and delivering stimulation in the form of pacing and shock therapy to the right ventricle.

Figure 6:
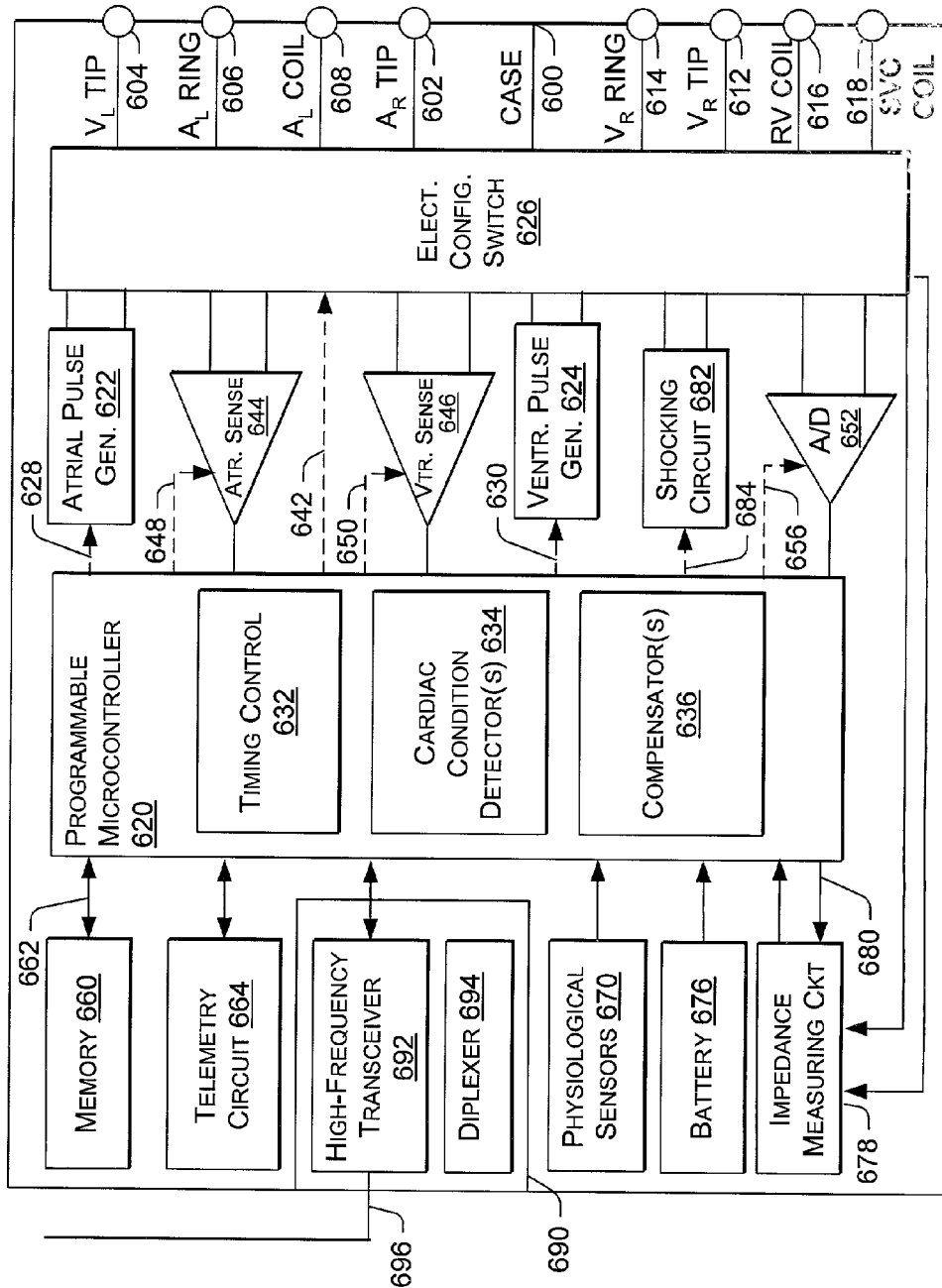
FIG. 6 is a functional block diagram of an exemplary implantable cardiac therapy device.

FIG. 6 shows an exemplary, simplified block diagram depicting various components of the ICTD 102. The ICTD 102 can be configured to perform one or more of a variety of functions including, for example, monitoring heart activity, monitoring patient activity, and treating fast and slow arrhythmias with stimulation therapy that includes cardioversion, defibrillation, and pacing stimulation. While a particular multi-chamber device is shown, it is to be appreciated and understood that this is done for illustration purposes.

The circuitry is housed in housing 600, which is often referred to as the "can", "case", "encasing", or "case electrode", and may be programmably selected to act as the return electrode for unipolar modes. Housing 600 may further be used as a return electrode alone or in combination with one or more of the coil electrodes for shocking purposes. Housing 600 further includes a connector (not shown) having a plurality of terminals 602, 604, 606, 608, 612, 614, 616, and 618 (shown schematically and, for convenience, the names of the electrodes to which they are connected are shown next to the terminals).

To achieve right atrial sensing and pacing, the connector includes at least a right atrial tip terminal ($A_R$ TIP) 602 adapted for connection to the atrial tip electrode 502. To achieve left chamber sensing, pacing, and shocking, the connector includes at least a left ventricular tip terminal ($V_L$ TIP) 604, a left atrial ring terminal ($A_L$ RING) 606, and a left atrial shocking terminal ($A_L$ COIL) 608, which are adapted for connection to the left ventricular ring electrode 504, the left atrial ring electrode 506, and the left atrial coil electrode 508, respectively. To support right chamber sensing, pacing, and shocking, the connector includes a right ventricular tip terminal ($V_R$ TIP) 612, a right ventricular ring terminal ($V_R$ RING) 614, a right ventricular shocking terminal (RV COIL) 616, and an SVC shocking terminal (SVC COIL) 618, which are adapted for connection to the right ventricular tip electrode 510, right ventricular ring electrode 512, the RV coil electrode 514, and the SVC coil electrode 516, respectively.

At the core of the ICTD 102 is a programmable microcontroller 620 that controls various operations of the ICTD, including cardiac monitoring and stimulation therapy. Microcontroller 620 includes a microprocessor (or equivalent control circuitry), RAM and/or ROM memory, logic and timing circuitry, state machine circuitry, and I/O circuitry. Microcontroller 620 includes the ability to process or monitor input signals (data) as controlled by a program code stored in a designated block of memory. Any suitable microcontroller 620 may be used. The use of microprocessor-based control circuits for performing timing and data analysis functions are well known in the art.

For discussion purposes, microcontroller 620 is illustrated as including timing control circuitry 632 to control the timing of the stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, and so on. Microcontroller 220 may further include various types of cardiac condition detectors 634 (e.g., an arrhythmia detector, a morphology detector, etc.) and various types of compensators 636 (e.g., orthostatic compensator, syncope response module, etc.). These components can be utilized by the device 102 for determining desirable times to administer various therapies. The components 632-636 may be implemented in hardware as part of the microcontroller 620, or as software/firmware instructions programmed into the device and executed on the microcontroller 620 during certain modes of operation.

The ICTD 102 further includes an atrial pulse generator 622 and a ventricular pulse generator 624 that generate pacing stimulation pulses for delivery by the right atrial lead 108(1), the coronary sinus lead 108(2), and/or the right ventricular lead 108(3) via an electrode configuration switch 626. It is understood that in order to provide stimulation therapy in each of the four chambers of the heart, the atrial and ventricular pulse generators, 622 and 624, may include dedicated, independent pulse generators, multiplexed pulse generators, or shared pulse generators. The pulse generators 622 and 624 are controlled by the microcontroller 620 via appropriate control signals 628 and 630, respectively, to trigger or inhibit the stimulation pulses.

The electronic configuration switch 626 includes a plurality of switches for connecting the desired electrodes to the appropriate I/O circuits, thereby providing complete electrode programmability. Accordingly, switch 626, in response to a control signal 642 from the microcontroller 620, determines the polarity of the stimulation pulses (e.g., unipolar, bipolar, combipolar, etc.) by selectively closing the appropriate combination of switches (not shown).

Atrial sensing circuits 644 and ventricular sensing circuits 646 may also be selectively coupled to the right atrial lead 108(1), coronary sinus lead 108(2), and the right ventricular lead 108(3), through the switch 626 to detect the presence of cardiac activity in each of the four chambers of the heart. Accordingly, the atrial (ATR. SENSE) and ventricular (VTR. SENSE) sensing circuits, 644 and 646, may include dedicated sense amplifiers, multiplexed amplifiers, or shared amplifiers. Each sensing circuit 644 and 646 may further employ one or more low power, precision amplifiers with programmable gain and/or automatic gain control, bandpass filtering, and a threshold detection circuit to selectively sense the cardiac signal of interest. The automatic gain control enables the ICTD 102 to deal effectively with the difficult problem of sensing the low amplitude signal characteristics of atrial or ventricular fibrillation. Switch 626 determines the "sensing polarity" of the cardiac signal by selectively closing the appropriate switches. In this way, the clinician may program the sensing polarity independent of the stimulation polarity.

The outputs of the atrial and ventricular sensing circuits 644 and 646 are connected to the microcontroller 620 which, in turn, is able to trigger or inhibit the atrial and ventricular pulse generators 622 and 624, respectively, in a demand fashion in response to the absence or presence of cardiac activity in the appropriate chambers of the heart. The sensing circuits 644 and 646 receive control signals over signal lines 648 and 650 from the microcontroller 620 for purposes of controlling the gain, threshold, polarization charge removal circuitry (not shown), and the timing of any blocking circuitry (not shown) coupled to the inputs of the sensing circuits 644 and 646.

Cardiac signals are also applied to inputs of an analog-to-digital (A/D) data acquisition system 652. The data acquisition system 652 is configured to acquire intracardiac electrogram signals, convert the raw analog data into a digital signal, and store the digital signals for later processing and/or telemetric transmission to an external device 654. The data acquisition system 652 is coupled to the right atrial lead 108(1), the coronary sinus lead 108(2), and the right ventricular lead 108(3) through the switch 626 to sample cardiac signals across any pair of desired electrodes.

The data acquisition system 652 may be coupled to the microcontroller 620, or other detection circuitry, to detect an evoked response from the heart 106 in response to an applied stimulus, thereby aiding in the detection of "capture". Capture occurs when an electrical stimulus applied to the heart is of sufficient energy to depolarize the cardiac tissue, thereby causing the heart muscle to contract. The microcontroller 620 detects a depolarization signal during a window following a stimulation pulse, the presence of which indicates that capture has occurred. The microcontroller 620 enables capture detection by triggering the ventricular pulse generator 624 to generate a stimulation pulse, starting a capture detection window using the timing control circuitry 632 within the microcontroller 620, and enabling the data acquisition system 652 via control signal 656 to sample the cardiac signal that falls in the capture detection window and, based on the amplitude, determines if capture has occurred.

The microcontroller 620 is further coupled to a memory 660 by a suitable data/address bus 662, wherein the programmable operating parameters used by the microcontroller 620 are stored and modified, as required, in order to customize the operation of the implantable device 102 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 106 within each respective tier of therapy. With memory 660, the ICTD 102 is able to sense and store a relatively large amount of data (e.g., from the data acquisition system 652), which may transmitted to the external network of knowledge workers for subsequent analysis.

Operating parameters of the ICTD 102 may be non-invasively programmed into the memory 660 through a telemetry circuit 664 in telemetric communication with an external device, such as a programmer 110 or local transceiver 112. T he telemetry circuit 664 advantageously allows intracardiac electrograms and status information relating to the operation of the device 102 (as contained in the microcontroller 620 or memory 660) to be sent to the external devices.

The ICTD 100 can further include one or more physiologic sensors 670, commonly referred to as "rate-responsive" sensors because they are typically used to adjust pacing stimulation rate according to the exercise state of the patient. However, the physiological sensor 670 may further be used to detect changes in cardiac output, changes in the physiological condition of the heart, or diurnal changes in activity (e.g., detecting sleep and wake states, detecting position or postural changes, etc.). Accordingly, the microcontroller 620 responds by adjusting the various pacing parameters (such as rate, AV Delay, V-V Delay, etc.) at which the atrial and ventricular pulse generators, 622 and 624, generate stimulation pulses. While shown as being included within the device 102, it is to be understood that the physiologic sensor 670 may also be external to the device 102, yet still be implanted within or carried by the patient. Examples of physiologic sensors that may be implemented in device 102 include known sensors that, for example, sense respiration rate and/or minute ventilation, pH of blood, ventricular gradient, and so forth.

The ICTD 102 additionally includes a battery 676 that provides operating power to all of circuits shown in FIG. 2. If the device 102 is configured to deliver pacing or shocking therapy, the battery 676 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 2 V, for periods of 10 seconds or more). The battery 676 also desirably has a predictable discharge characteristic so that elective replacement time can be detected. As one example, the device 102 employs lithium/silver vanadium oxide batteries.

The ICTD 102 can further include magnet detection circuitry (not shown), coupled to the microcontroller 620, to detect when a magnet is placed over the device 102. A magnet may be used by a clinician to perform various test functions of the device 102 and/or to signal the microcontroller 620 that the external programmer is in place to receive or transmit data to the microcontroller 620 through the telemetry circuits 664.

The ICTD 102 further includes an impedance measuring circuit 678 that is enabled by the microcontroller 620 via a control signal 680. Uses for an impedance measuring circuit 678 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 678 is advantageously coupled to the switch 626 so that any desired electrode may be used.

In the case where the device 102 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 620 further controls a shocking circuit 682 by way of a control signal 684. The shocking circuit 682 generates shocking pulses of low (up to 0.5 Joules), moderate (0.5-10 Joules), or high energy (11 to 40 Joules), as controlled by the microcontroller 620. Such shocking pulses are applied to the patient's heart 106 through at least two shocking electrodes, and as shown in this implementation, selected from the left atrial coil electrode 508, the RV coil electrode 514, and/or the SVC coil electrode 516. As noted above, the housing 600 may act as an active electrode in combination with the RV coil electrode 514, or as part of a split electrical vector using the SVC coil electrode 516 or the left atrial coil electrode 508 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 Joules), delivered asynchronously (since R-waves may be too disorganized), and pertaining exclusively to the treatment of fibrillation. Accordingly, the microcontroller 620 is capable of controlling the synchronous or asynchronous delivery of the shocking pulses.

The ICTD 102 is further designed with the ability to support high-frequency wireless communication, typically in the radio frequency (RF) range. As illustrated in FIG. 2, the can 600 is configured with a secondary, isolated casing 690 that contains circuitry for handling high-frequency signals. Within this separate case 690 are a high-frequency transceiver 692 and a diplexer 694. High-frequency signals received by a dedicated antenna 696, or via leads 108, are passed to the transceiver 692. Due to the separate casing region 690, the transceiver handles the high-frequency signals in isolation apart from the cardiac therapy circuitry. In this manner, the high-frequency signals can be safely handled, thereby improving telemetry communication, without adversely disrupting operation of the other device circuitry.

Exemplary Computing Device

Figure 7:
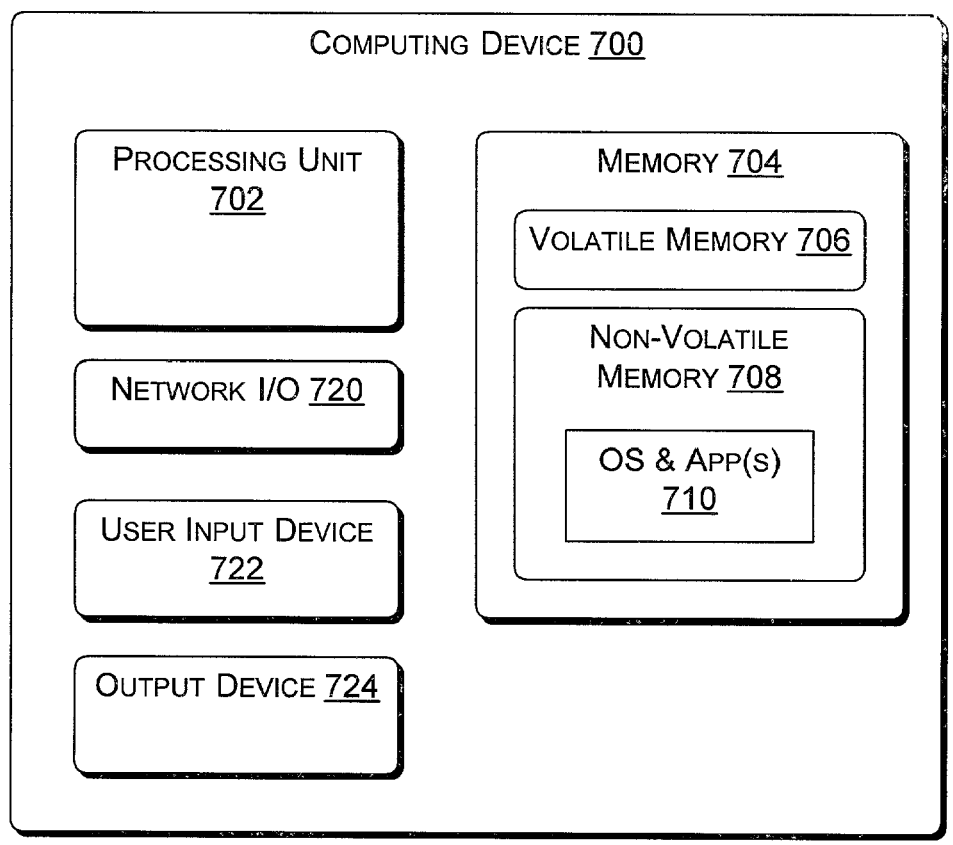
FIG. 7 is a functional block diagram of an exemplary computing device that may be used in the computing systems of the cardiac therapy network architecture.

FIG. 7 shows an exemplary computing device 700 employed in the computing systems of the cardiac therapy network architecture 100. It includes a processing unit 702 and memory 704. Memory 704 includes both volatile memory 706 (e.g., RAM) and non-volatile memory 708 (e.g., ROM, EEPROM, Flash, disk, optical discs, persistent storage, etc.). An operating and system and various application programs 710 are stored in non-volatile memory 708. When a program is running, various instructions are loaded into volatile memory 706 and executed by processing unit 702. Examples of possible applications that may be stored and executed on the computing device include the knowledge worker specific applications 206 shown in FIG. 2.

The computing device 700 may further be equipped with a network I/O connection 720 to facilitate communication with a network. The network I/O 720 may be a wire-based connection (e.g., network card, modem, etc.) or a wireless connection (e.g., RF transceiver, Bluetooth device, etc.). The computing device 700 may also include a user input device 722 (e.g., keyboard, mouse, stylus, touch pad, touch screen, voice recognition system, etc.) and an output device 724 (e.g., monitor, LCD, speaker, printer, etc.).

Various aspects of the methods and systems described throughout this disclosure may be implemented in computer software or firmware as computer-executable instructions. When executed, these instructions direct the computing device (alone, or in concert with other computing devices of the system) to perform various functions and tasks that enable the cardiac therapy network architecture 100.

High-Frequency Packaging Design

One feature of the network architecture is an improved transmission range between the ICTD 102 and the local transceiver 112 and/or programmer 116. Longer range telemetry is made possible by employing high-frequency signals, such as RF signals. However, since such high-frequency signals may interfere with detection of cardiac conditions, the ICTD 102 is specially designed to isolate the high-frequency circuitry from the cardiac therapy circuitry.

Figure 8:
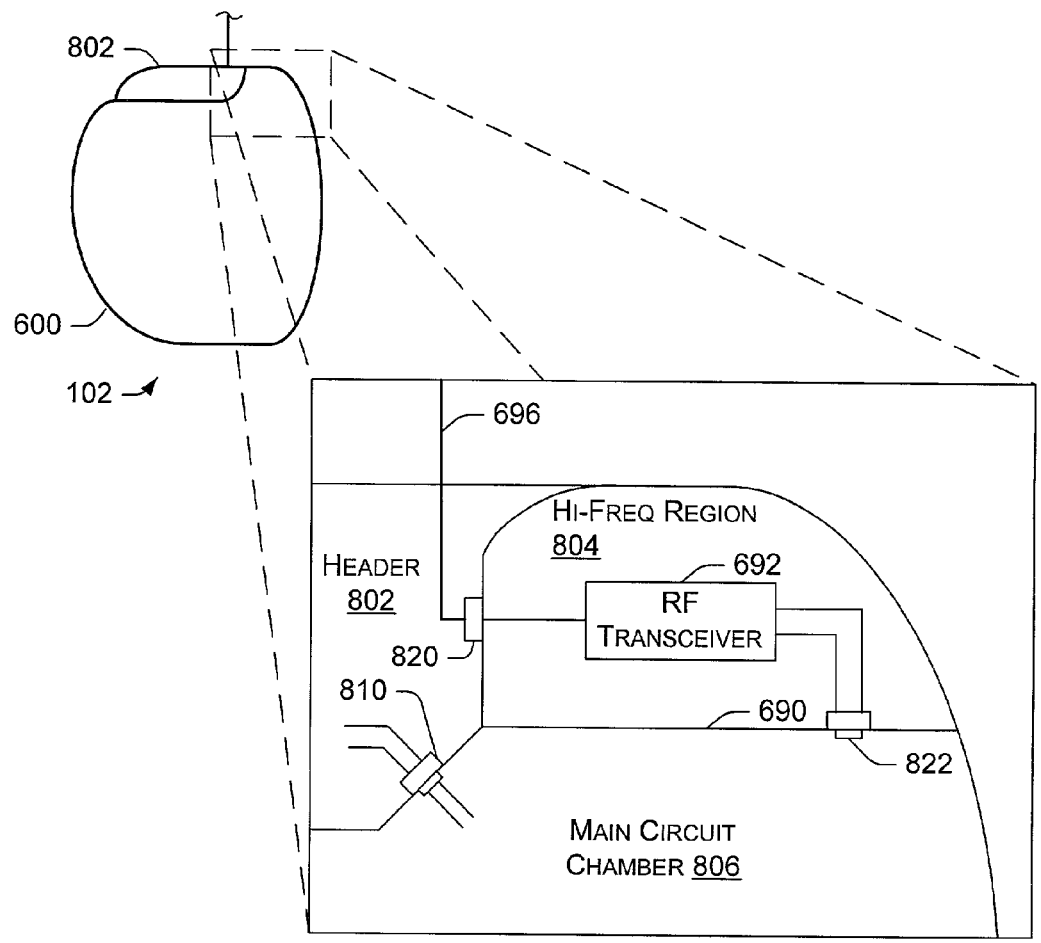
FIG. 8 is a diagrammatic illustration of an ICTD with packaging that defines dual isolated chambers, one for housing high-frequency circuitry and a second for housing the ICTD monitoring and stimulation circuitry.

FIG. 8 shows an exemplary ICTD 102 that is equipped with additional high-frequency packaging and circuitry to support long range telemetry. Long range telemetry allows communication with implanted medical devices at distances greater than conventional "wand telemetry" of a few inches. Generally, ICTD 102 is designed with a hermetically shielded can 600 to prevent electromagnetic interference (EMI) from disrupting operation of the sensing and/or stimulation circuitry. The can 600 employs one or more filters to block high-frequency transmissions (e.g., radio frequencies) and other sources of EMI (e.g., automobile engines). As an example, the filters typically remove signals above 1 MHz. Thus, the can 600 prevents penetration of high frequencies and tries to limit communication to the low frequency ranges of less than 200 KHz.

With conventional short-range telemetry communications, signals sent from a programmer (e.g., offline programmer 110) to the implanted device are transmitted at approximately 36 KHz, and data is transmitted back from the implanted device to the programmer at approximately 8 KHz. A feed-through filter 810 filters signals passed from the header 802 to the main circuitry chamber 806. It filters, for example, signals above 1 MHz. Low range signals received from the external programmer via conventional short-range telemetry (e.g., magnetic couplings from wand to device) are filtered through this feed-through filter 810.

The ICTD 103 has a header region 802 that holds the connection terminals for leads 108(1)-(3). Adjacent the header is a separate and frequency-isolated packaging region 804, defined in part by can wall 690, which contains circuitry for handling high-frequency signals. As one example, the interior can wall 690 is constructed of titanium, similar to the exterior can; alternatively, it could be made from another conducting metal. The high-frequency packaging region can be thought of as a separate can that isolates the RF components from the main circuitry. The dual-can design enables the ICTD to handle high-frequency signals carrying data and control information in one can of the device without disrupting operation of the main circuitry in the second can of the device.

An RF transceiver 692 is positioned within the high-frequency packaging region 804. Signals received from an antenna 696 are passed through an unfiltered feed-through 820 into the RF transceiver 692. The transceiver is capable of receiving and transmitting high-frequency signals, such as those found in the radio frequency range. As one example range, the transceiver handles signals within 400 to 900 MHz. The RF transceiver 692 is coupled to the internal circuitry within the main circuitry chamber 806 via a feed-through filter 822. Data, power, control, and other types of information can be exchanged between the transceiver 692 and the circuitry using the feed-through filter 822. The metal shield encompassing the high-frequency region 804 blocks spurious signals emanating from the RF transceiver 692 from interfering with the sensing and pacing functions of the main circuitry.

Although the high-frequency region 804 is shown adjacent to header 802 and above the main circuit chamber 806, encapsulated by the outer can wall of the device and the interior wall 690, the region 804 may be located in any number of places. It may be, for example, implemented as an isolated cavity contained entirely within the main circuit chamber 806. Alternatively, it may be constructed external to the ICTD 102, but employ part of the exterior can 600 to define a portion of the region. Another possible implementation is to construct the high-frequency region as a separate implantable can that is in communication with the ICTD, but implanted apart from the ICTD 102.

The antenna for transmitting and receiving the high-frequency data signals may be implemented in a number of ways. One approach is to employ a dedicated antenna positioned within the header region 802. Another approach is to employ a dedicated antenna that extends beyond the header region 802, such as antenna 696 illustrated in FIG. 8. A third approach is to integrate the antenna into the can 600. Still another approach is to use one or more of the leads 108(1)-(3) as the antenna.

Figure 9:
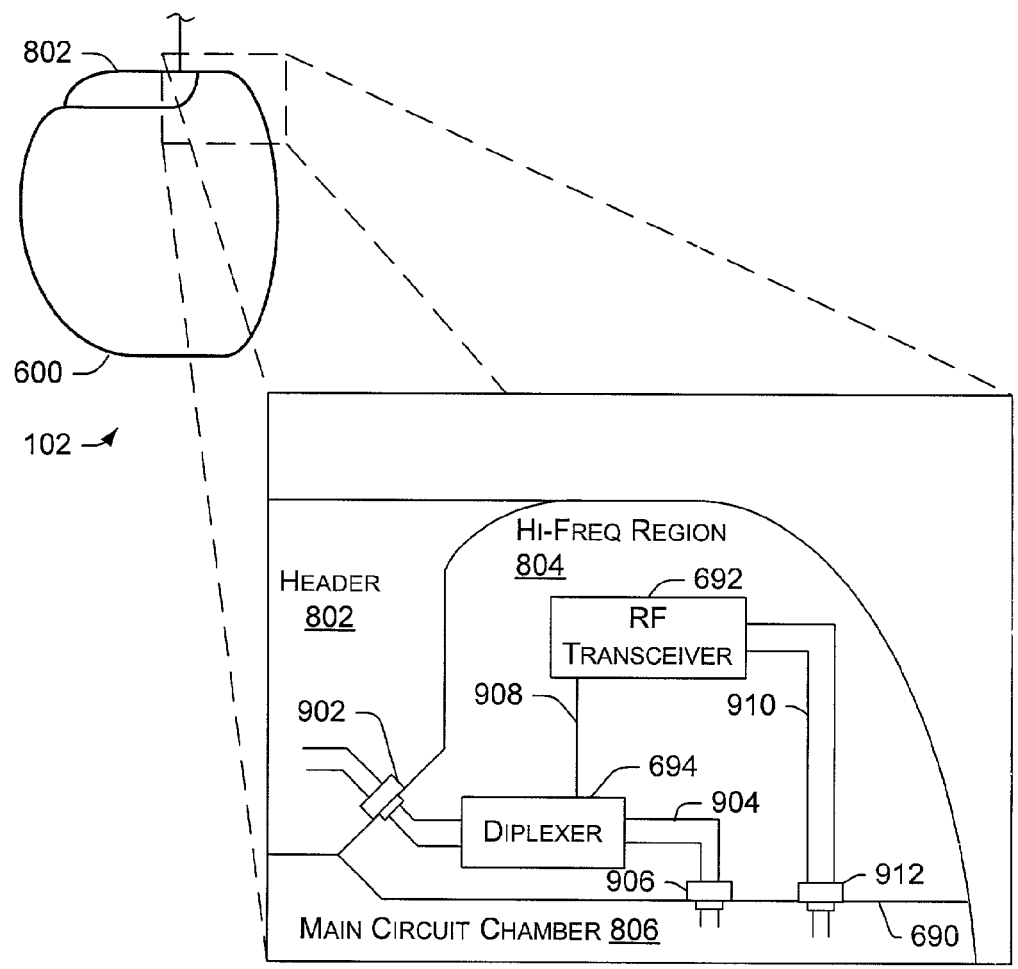
FIG. 9 is a diagrammatic illustration of an ICTD similar to FIG. 8, but further including a diplexer circuit in the high-frequency chamber.

FIG. 9 shows the latter approach in which the leads are employed as the antenna. In this implementation, the signals from the lead are passed through an unfiltered feed-through 902 to a diplexer 694. The diplexer 694 allows two signals of different frequencies to be transmitted along the same conductor and separates the signal frequencies onto two different connections. In the illustrated implementation, the diplexer 694 is designed to direct RF signals to the RF transceiver 692 and the electrocardiograph (ECG) signals to the main circuitry in chamber 806.

The diplexer's first connection 904 leads to a feed-through 906 into the ICTD circuitry within the chamber 806. The diplexer 694 filters this first connection to pass low frequencies of the ECG signal. High frequencies are blocked and therefore do not interfere with the sensing of the ECG.

A second connection 908 on the diplexer 694 connects to the RF transceiver 692. The filter on this connection is tuned to the carrier frequency of the transceiver 692. Thus, low frequency signals, such as the ECG, are blocked. The RF transceiver 692 extracts the data and control instructions from the carrier frequency and passes the information to the ICTD circuitry via connections 910 and a feed-through 912. The feed-through 912 can be filtered to prevent any high-frequency components from entering the main circuit chamber 806. Power is supplied to the RF transceiver 692 and diplexer 694 from the battery in the main circuitry chamber via the feed-throughs 902 and 912.

When transmitting, the transceiver 692 generates signals that are conducted out through the diplexer 694 to the leads. The RF signals are not conducted back into the main circuitry. Similarly, any pacing stimuli are conducted out to the leads via diplexer 694, without affecting the RF circuitry.

The dual-chamber design provides optimal isolation. With the diplexer, dual enclosure regions, and filtered feed-throughs, the design isolates the main monitoring/stimulating circuitry from RF interference emanated from the diplexer or transceiver, while simultaneously allowing long-range RF telemetry communication. Additionally, the design allows the leads to be used as both stimulation/sensing leads and as a radio frequency (RF) antenna, without causing interference to the monitoring and/or stimulation functions.

Exemplary Diplexer

The diplexer 694 can be constructed in several ways. One implementation is described for discussion purposes, but many other alternatives are possible. The implementation described below is formed with inductors and capacitors to illustrate the basic concept of splitting high and low frequency signals. It is noted that other forms of bandpass and/or bandstop filters may be used, as well as more complex filters that selectively pass and block the desired frequencies or bands of frequencies.

Figure 10:
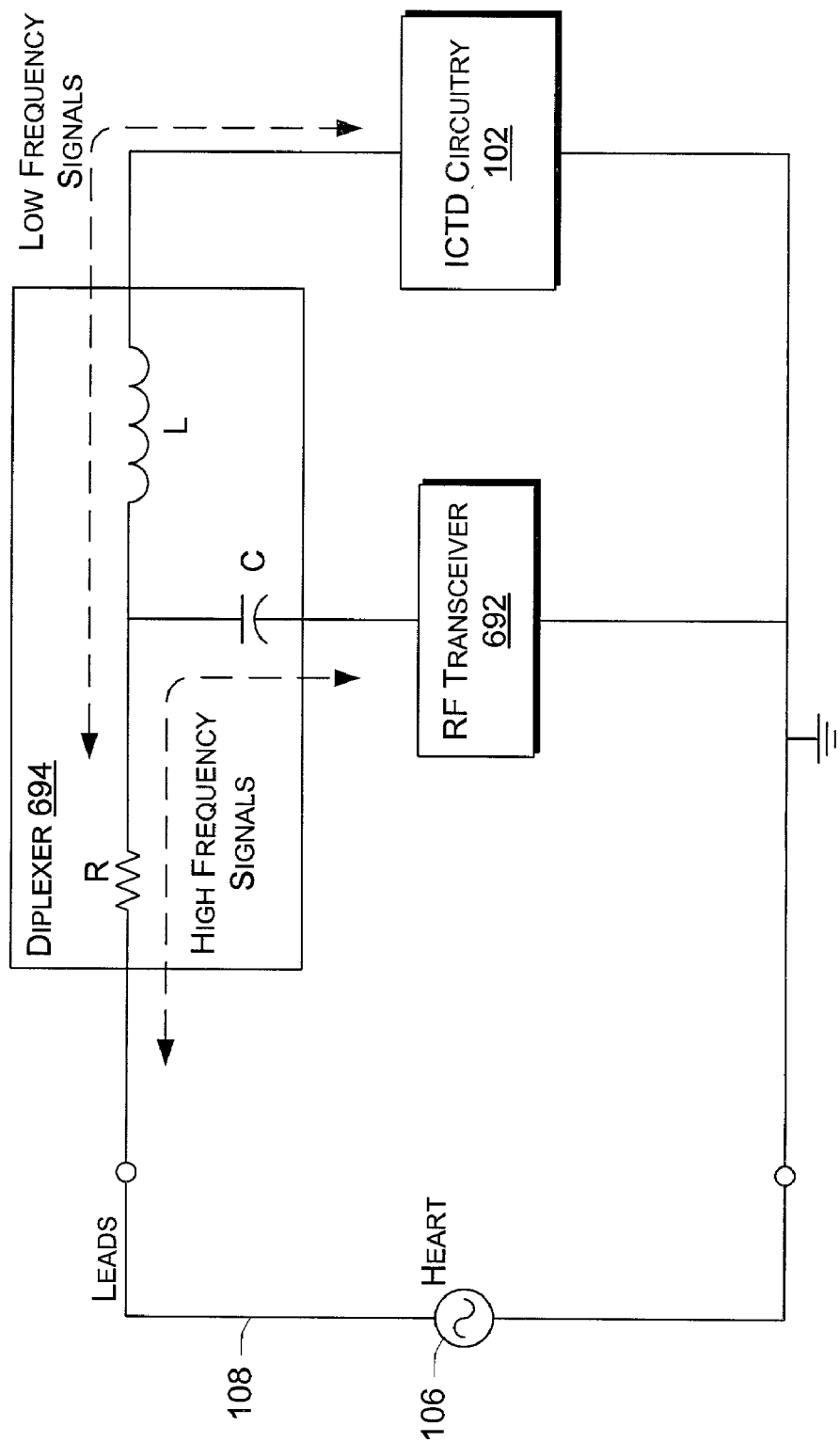
FIG. 10 is a circuit diagram of an exemplary diplexer employed in the ICTD of FIG. 9.

FIG. 10 shows an exemplary diplexer 694 connected to heart 106 via leads 108, and to the RF transceiver 692 and ICTD circuitry 102. The leads 108 are multi-functional. They are used to conduct low-frequency cardiac signals from the heart 106 and apply pacing and other stimulation therapies to the heart 106. The leads also function as an antenna to transmit and receive high-frequency signals. Both high- and low-frequency signals are passed to the diplexer 694.

The diplexer 694 includes a resistor R, a capacitor C, and an inductor L. These components are arranged in an RCL configuration so that high-frequency signals are passed through the resistor-capacitor (RC) branch to the RF transceiver 692 and low-frequency signals are passed through the resistor-inductor (RL) branch to the ICTD circuitry 102. The values of the resistor, capacitor, and inductor are chosen to define desired filter breakover points at which frequencies above a certain threshold pass to the RF transceiver 692 while being blocked from the ICTD circuitry 102, and frequencies below the threshold pass to the ICTD circuitry 102 while being blocked from the RF transceiver 692.

Figure 11:
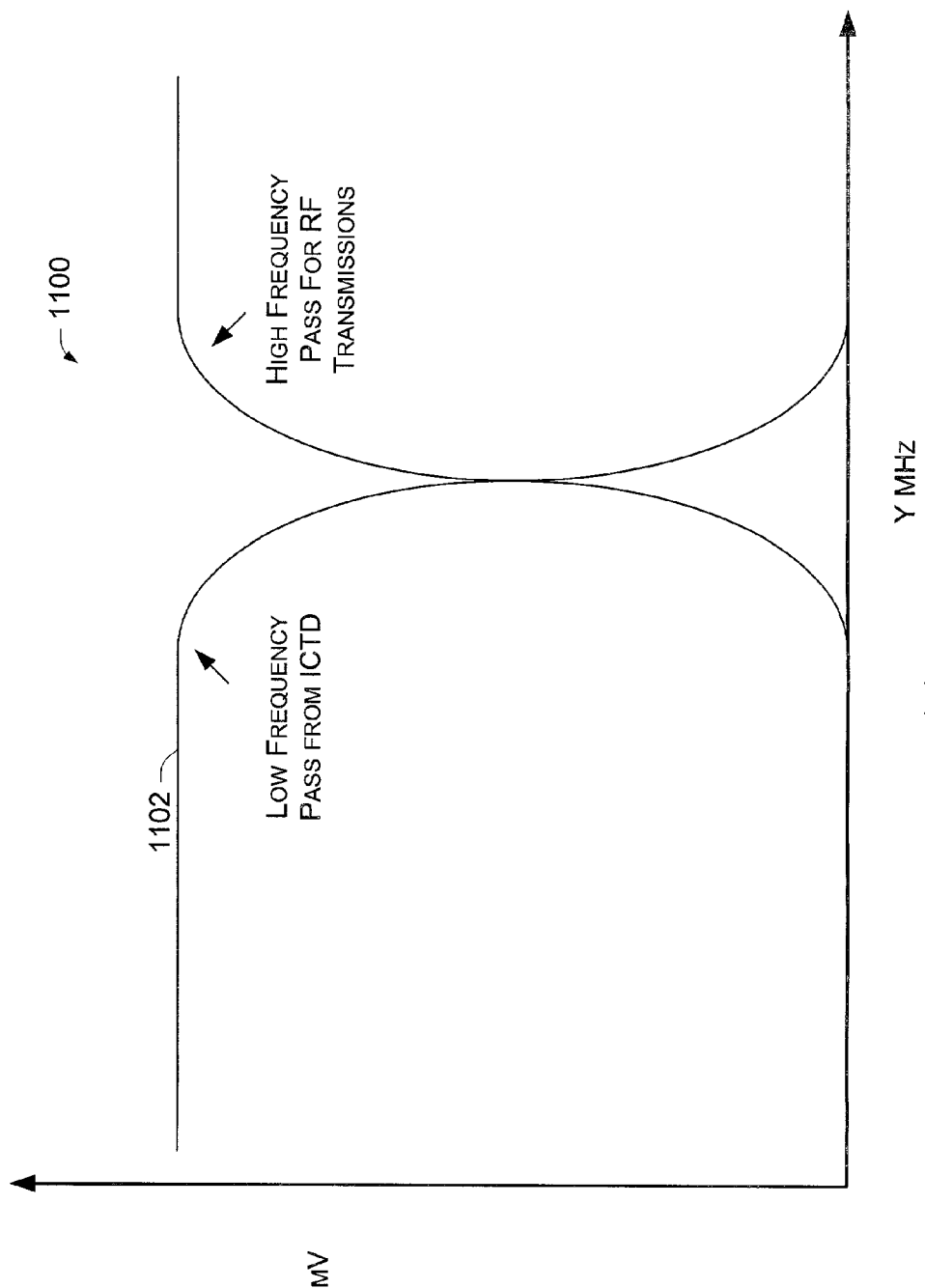
FIG. 11 is a frequency plot illustrating the filter characteristics of the diplexer of FIG. 10.

FIG. 11 shows a frequency chart 1100 with example filter characteristics achieved by the diplexer 694 of FIG. 10. The diplexer 694 establishes a low pass filter 1102 that passes low-frequency signals of less than approximately Y MHz, while simultaneously establishing a high pass filter that passes high-frequency signals of more than approximately Y MHz. As an example, Y may be chosen to be approximately 1 to 10 MHz.

Operation

Figure 12:
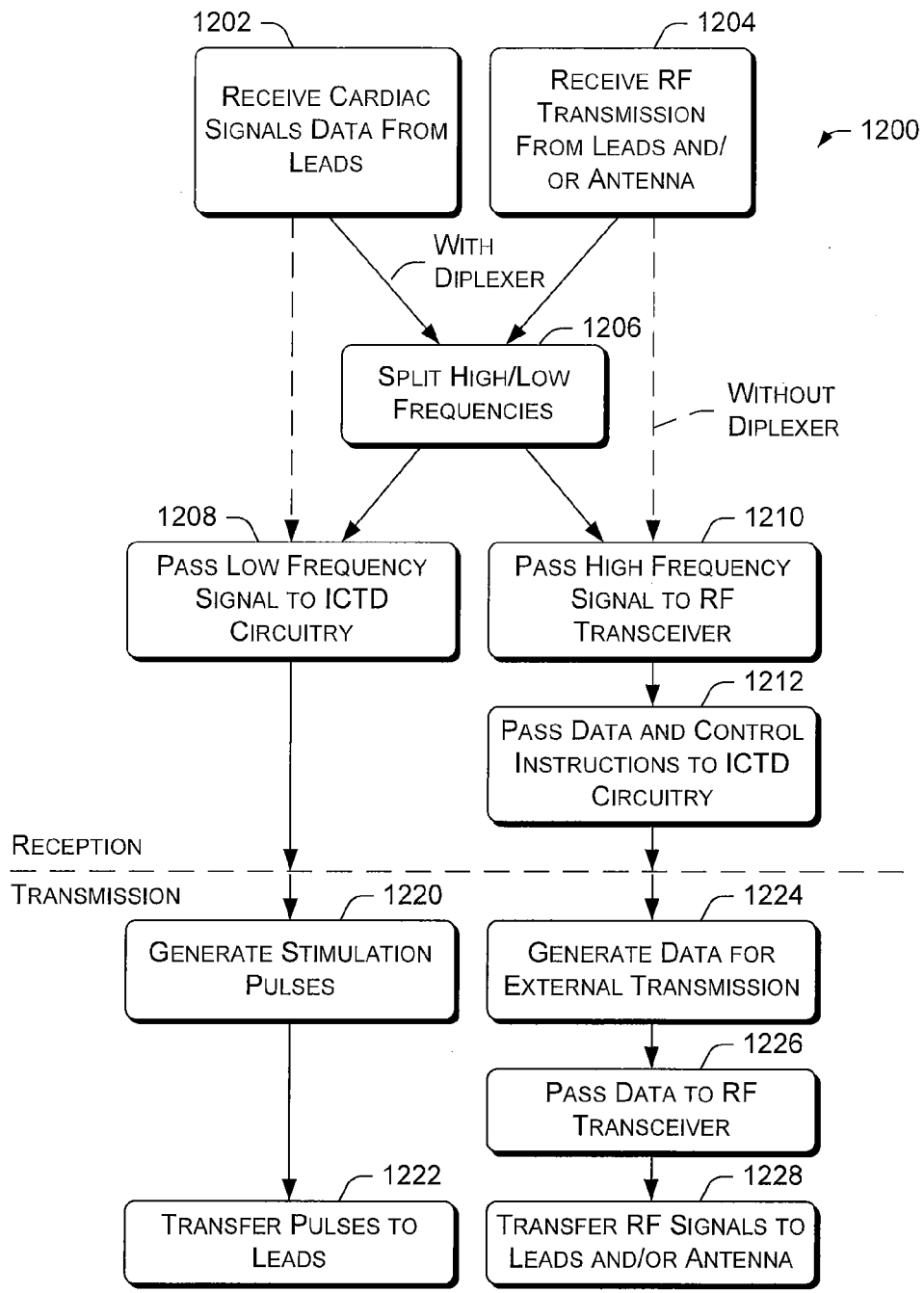
FIG. 12 is a flow diagram of a method for operating the dual chambered ICTD.

FIG. 12 shows a process 1200 for operating the ICTD 102 with high-frequency circuitry. Aspects of this process may be implemented in hardware, firmware, or software, or a combination thereof. The process may be viewed in two phases: (1) a reception phase in which both low- and high-frequency signals are received at the ICTD 102, and (2) a transmission phase in which the ICTD 102 transmits high-frequency signals and/or applies stimulation therapy. The dashed dividing line in FIG. 12 pictorially segments these phases.

At block 1202, the implantable cardiac therapy device 102 receives low-frequency cardiac signals from leads 108(1)-(3). Concurrently, at block 1204, the ICTD 102 receives RF transmissions from the leads 108(1)-(3) and/or a dedicated antenna (e.g., antenna 696). The RF transmission originates from some external device, such as the local transceiver 112 in FIG. 1. When a diplexer 694 is present (e.g., the implementation shown in FIG. 9), the low-frequency cardiac signals and high-frequency RF transmissions are sent to the high-frequency region 804 of the ICTD housing for separation by the diplexer. At block 1206, the diplexer effectively splits the high and low frequency signals. The low frequency cardiac signals are passed to the ICTD circuitry via a feed-through (block 1208) and the high-frequency signals are conducted within the high-frequency region 804 to the RF transceiver 692 (block 1210). The RF transceiver 692 receives the RF signals, extracts the data and control instructions, and passes the information to the ICTD circuitry via a filtered feed-through (block 1212).

At this point, the ICTD 102 may process the cardiac data, as well as the various data and control instructions received via RF signals. The data and control instructions may be produced by any number of sources-including healthcare providers, clinical groups, and so on-and routed to the ICTD via network 110 (see FIG. 1). The information may be used to program the device, modify therapies, or query data.

During the transmission phase, the ICTD 102 is able to apply stimulation therapy to the heart 106 and/or transmit information back out to the network of knowledge workers. In the former case, the circuitry generates stimulation pulses (e.g., pacing, defibrillation shock, etc.) at block 1220 and transfers the pulses to one or more of the leads 108(1)-(3) at block 1222. In the latter case, the circuitry generates information for external transmission (block 1224). This information is passed via the feed-through into the isolated high-frequency region 804 and to the RF transceiver 692 (block 1226). The transceiver 692 creates RF signals that are conducted out to the leads and/or antenna for transmission back to the local transceiver 112.

CONCLUSION

Although the invention has been described in language specific to structural features and/or methodological acts, it is to be understood that the subject matter defined in the appended claims is not necessarily limited to the specific features or acts described. Rather, the specific features and acts are disclosed as exemplary forms of implementing the claimed invention.

The invention claimed is:

1. An implantable cardiac therapy device comprising:
    cardiac therapy circuitry configured to perform at least one of (1) monitoring cardiac activity or (2) administering stimulation therapy;
    a high-frequency transceiver adapted to transmit and receive communication signals via an antenna to enable high frequency communication; and
    an enclosed casing to house both the cardiac therapy circuitry and the high-frequency transceiver, while isolating the high-frequency transceiver from the cardiac therapy circuitry,
    wherein the casing comprises a first chamber to house the cardiac therapy circuitry; and
    a second chamber to house the high-frequency transceiver.

2. An implantable cardiac therapy device as recited in claim 1, wherein the communication circuitry comprises an RF transceiver.

3. An implantable cardiac therapy device as recited in claim 1, wherein the antenna is integrated into the casing.

4. An implantable cardiac therapy device as recited in claim 1, wherein the casing has a header to which conductive leads can be connected, the antenna residing in the header of the casing.

5. An implantable cardiac therapy device as recited in claim 1, wherein the casing has a header to which conductive leads can be connected, and wherein the implantable cardiac therapy device further comprises
    a diplexer coupled to receive high-frequency signals and low-frequency signals from the leads and to split the high-frequency signals from the low-frequency signals, the diplexer passing the high-frequency signals to the high-frequency transceiver and the low-frequency signals to the cardiac therapy circuitry.

6. A cardiac network system comprising:
    the implantable cardiac therapy device as recited in claim 1; and
    a computing network to link one or more computing systems to the implantable cardiac therapy device.

* * * * *